(12) United States Patent
Borries

(10) Patent No.: US 10,213,312 B2
(45) Date of Patent: Feb. 26, 2019

(54) HEATED BOLT FOR MODULAR HIP STEM

(71) Applicant: Zimmer, Inc., Warsaw, IN (US)

(72) Inventor: Paul Borries, Columbia City, IN (US)

(73) Assignee: Zimmer, Inc., Warsaw, IN (US)

( * ) Notice: Subject to any disclaimer, the term of this patent is extended or adjusted under 35 U.S.C. 154(b) by 25 days.

(21) Appl. No.: 14/787,853

(22) PCT Filed: May 15, 2014

(86) PCT No.: PCT/US2014/038202
§ 371 (c)(1),
(2) Date: Oct. 29, 2015

(87) PCT Pub. No.: WO2014/189765
PCT Pub. Date: Nov. 27, 2014

(65) Prior Publication Data
US 2016/0106543 A1 Apr. 21, 2016

Related U.S. Application Data

(60) Provisional application No. 61/826,742, filed on May 23, 2013.

(51) Int. Cl.
*A61F 2/36* (2006.01)
*A61F 2/30* (2006.01)

(52) U.S. Cl.
CPC .......... *A61F 2/3609* (2013.01); *A61F 2/3094* (2013.01); *A61F 2002/30077* (2013.01);
(Continued)

(58) Field of Classification Search
CPC .................. A61F 2/3609; A61F 2/3662; A61F 2002/3652; A61F 2002/3674; A61F 2002/3694
See application file for complete search history.

(56) References Cited

U.S. PATENT DOCUMENTS 3,846,846 A * 11/1974 Fischer ............... A61F 2/3662
411/33
5,030,236 A * 7/1991 Dean ...................... A61F 2/367
433/201.1

(Continued)

FOREIGN PATENT DOCUMENTS

GB      662302 A    12/1951
GB    1451443 A    10/1976

(Continued)

OTHER PUBLICATIONS

"European Application Serial No. 14732484.2, Response filed Aug. 8, 2016 to Communication pursuant to Rules 161(1) and 162 EPC dated Jan. 27, 2016", 9 pgs.

(Continued)

*Primary Examiner* — Bruce E Snow
*Assistant Examiner* — Melissa Hoban
(74) *Attorney, Agent, or Firm* — Schwegman Lundberg & Woessner, P.A.

(57) ABSTRACT

During hip replacement surgery, a practitioner can attach a distal stem to a femur of the patient and can then fixedly attach a proximal body to the distal stem using a bolt. Prior to tightening, the bolt can be heated to an elevated temperature greater than average human core body temperature. The practitioner can tighten the bolt to a specified torque while the bolt is at the elevated temperature. After tightening, the bolt cools to average human core body temperature and experiences a tensile stress due to the effects of thermal expansion. The tensile stress in the bolt produces a compressive force between the distal stem and the proximal body. The compressive force can increase the attachment strength of the bolt to the distal stem and the proximal body, beyond what can be achieved by solely torquing the bolt to (Continued)

the specified level during surgery without first heating the bolt.

19 Claims, 8 Drawing Sheets

(52) U.S. Cl.
CPC .............. *A61F 2002/30604* (2013.01); *A61F 2002/3652* (2013.01)

(56) References Cited

U.S. PATENT DOCUMENTS

| | | | | |
|---|---|---|---|---|
| 5,429,638 | A * | 7/1995 | Muschler | A61B 17/7216 606/60 |
| 6,034,295 | A * | 3/2000 | Rehberg | A61B 17/72 433/201.1 |
| 6,240,323 | B1 * | 5/2001 | Calenzo, Sr. | A61N 1/0456 600/372 |
| 2002/0183851 | A1 * | 12/2002 | Spiegelberg | A61B 17/8802 623/22.12 |
| 2003/0040806 | A1 * | 2/2003 | MacDonald | A61B 5/4839 623/23.49 |
| 2004/0117024 | A1 * | 6/2004 | Gerbec | A61F 2/30734 623/18.11 |
| 2005/0137711 | A1 | 6/2005 | Southworth et al. | |
| 2006/0265026 | A1 * | 11/2006 | Madjar | A61C 8/0006 607/51 |
| 2008/0021465 | A1 * | 1/2008 | Shadduck | A61B 17/7002 606/279 |
| 2008/0172107 | A1 * | 7/2008 | McGinnis | A61N 1/326 607/51 |
| 2010/0023057 | A1 * | 1/2010 | Aeschlimann | A61B 17/0401 606/246 |
| 2012/0130502 | A1 | 5/2012 | Podolsky et al. | |
| 2013/0253595 | A1 * | 9/2013 | Zucherman | A61B 17/8625 606/305 |
| 2014/0194328 | A1 * | 7/2014 | Alessi | C04B 38/009 507/269 |
| 2016/0158980 | A1 * | 6/2016 | Fitzpatrick | B29C 45/03 264/328.15 |
| 2016/0279854 | A1 * | 9/2016 | Fitzpatrick | B29C 35/0805 |

FOREIGN PATENT DOCUMENTS

| | | |
|---|---|---|
| JP | 09216133 A | 8/1997 |
| JP | 09317734 A | 12/1997 |
| WO | WO-9513757 A1 | 5/1995 |
| WO | WO-2014189765 A1 | 11/2014 |

OTHER PUBLICATIONS

"International Application Serial No. PCT/US2014/038202, International Preliminary Report on Patentability dated Dec. 3, 2015", 7 pgs.

"International Application Serial No. PCT/US2014/038202, International Search Report dated Aug. 7, 2014", 4 pgs.

"International Application Serial No. PCT/US2014/038202, Written Opinion dated Aug. 7, 2014", 5 pgs.

"European Application Serial No. 14732484.2, Communication Pursuant to Article 94(3) EPC dated May 29, 2018", 4 pgs.

"European Application Serial No. 14732484.2, Response filed Oct. 3, 2018 to Communication Pursuant to Article 94(3) EPC dated May 29, 2018", 15 pgs.

* cited by examiner

HEATED BOLT FOR MODULAR HIP STEM

CLAIM OF PRIORITY

This application is a U.S. National Stage Filing under 35 U.S.C. 371 from International Application No. PCT/US2014/038202, filed on May 15, 2014, and published as WO 2014/189765 A1 on Nov. 27, 2014, which claims the benefit of U.S. Provisional Patent Application Ser. No. 61/826,742, filed on May 23, 2013, the benefit of priority of each of which are claimed hereby, and which are incorporated by reference herein in their entirety.

BACKGROUND

A human hip joint connects a femur (sometimes referred to as a thigh bone) to an acetabulum (sometimes referred to as a hip socket) of the pelvis. Hip joints support the weight of a human body, and are important for retaining balance.

Some types of injury, disease, or degeneration can produce pain and/or restricted motion in a hip joint. One treatment for certain types of damage to a hip joint is surgery. For relatively mild hip damage, the hip can be surgically repaired. For more severe damage, the hip can be surgically replaced.

OVERVIEW

In hip replacement surgery, a practitioner can remove the natural head and neck of a femur and replace them with a metallic hip prosthesis. This prosthesis can include two elements: a distal stem for fixation into the femur, and a proximal body for fixation in the metaphysis of the femur. In a modular hip stem, the proximal body and the distal stem can be adjustable with respect to each other. The prosthesis can also include a neck for replacing the natural femoral neck; this neck can be part of the proximal body, or can be a separate element that is adjustable with respect to the proximal body and the distal stem.

The distal stem can be first attached to the femur. Once the distal stem is attached, the practitioner can adjust the orientation of the proximal body with respect to the distal stem. The prosthesis can include adjustments for anteversion (e.g., the degree to which the femur is rotated forward toward the front of the body or backward toward the back of the body), offset (e.g., the left-right distance of the femur from the centerline of the body), and height (e.g., the length of the femur), for example. Once the proximal body is suitably oriented with respect to the distal stem, the practitioner can fixedly attach the proximal body to the distal stem with a bolt. During surgery, the practitioner can tighten the bolt to a specified torque. Once tightened, the bolt remains in place beyond the end of the surgery, and continues to attach the proximal body to the distal stem for as long as the artificial hip is installed within the patient.

It is important that the proximal body and the distal stem remain firmly attached over time. As such, in various instances, it can be desirable to increase the strength of the attachment provided by the bolt without over-torquing and causing damage to one or more elements within the modular hip stem.

Prior to tightening, the bolt can be heated to an elevated temperature greater than average human core body temperature. The practitioner can tighten the bolt to the specified torque, while the bolt is at the elevated temperature. After tightening, the bolt cools to average human core body temperature. If the bolt were unattached during cooling, it would longitudinally shrink due to the effects of thermal expansion. Because the bolt is attached at an elevated temperature and cools in place, it experiences a tensile stress due to the effects of thermal expansion. The tensile stress in the bolt produces a compressive force between the distal stem and the proximal body. The compressive force can increase the attachment strength of the bolt to the distal stem and the proximal body, beyond what can be achieved by solely torquing the bolt to the specified level during surgery without first heating the bolt.

This Overview is intended to provide examples of subject matter of the present patent document. It is not intended to provide an exclusive or exhaustive explanation of the invention. The Detailed Description below is included to provide further information about the present modular hip stems and the corresponding methods.

BRIEF DESCRIPTION OF THE DRAWINGS

In the drawings, which are not necessarily drawn to scale, like numerals can describe similar components in different views. The drawings illustrate generally, by way of example, but not by way of limitation, various embodiments discussed in the present patent document.

DETAILED DESCRIPTION

When surgically installing a modular hip stem, a practitioner can choose a distal stem and a proximal body from a kit. The kit can include various options for tapers, surface finishes, geometries, and lengths. In general, for a modular hip stem kit, the various configurations for the distal stem are compatible with the various configurations for the proximal body, and can include a common interface. For the example distal stems and proximal bodies described below and shown in the figures, it will be understood that other suitable options can also be used for tapers, surface finishes, geometries, and lengths.

Figure 1:
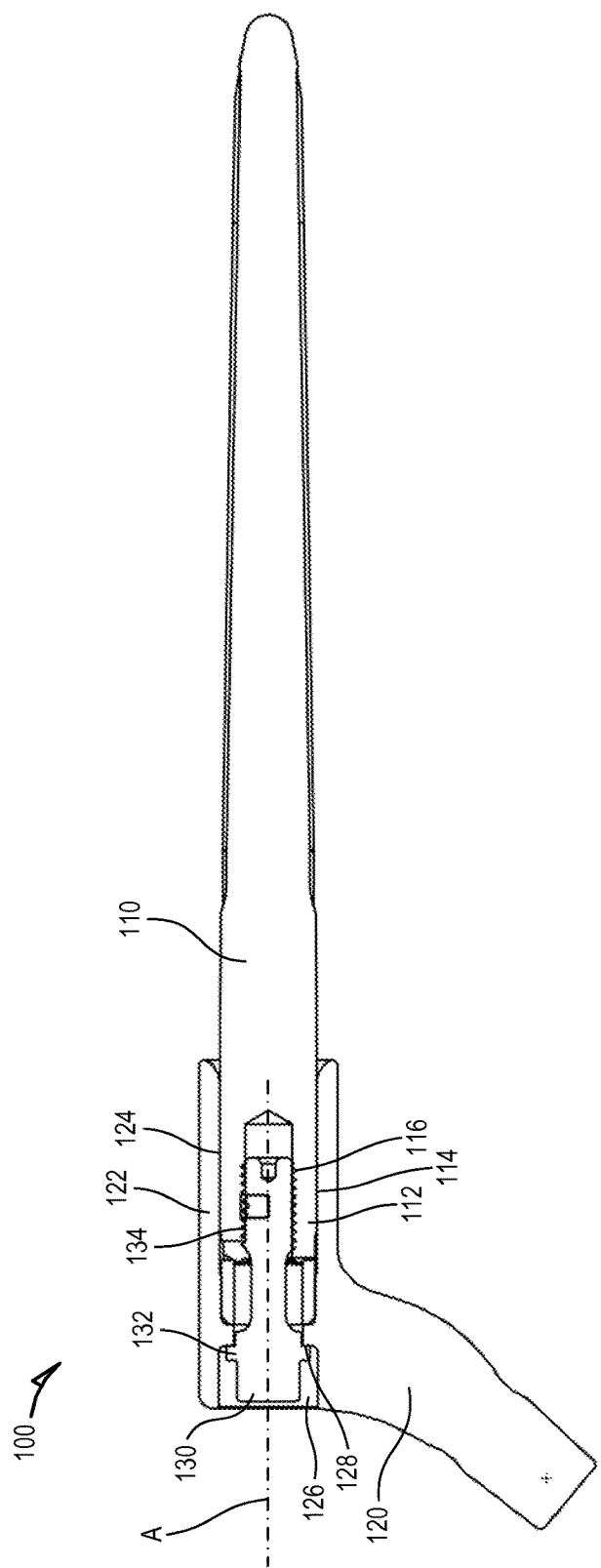
FIG. 1 is a side-view drawing of an exemplary modular hip stem, including a distal stem connected to a proximal body using a bolt. The interface between the distal stem and the proximal body is cylindrical.

FIG. 1 is a side-view drawing of an exemplary modular hip stem 100. The modular hip stem 100 includes an exemplary distal stem 110 connected to an exemplary proximal body 120 using a bolt 130.

The distal stem 110 includes an annular projection 112 at its proximal end. The annular projection 112 has an exterior surface 114 that is cylindrical in shape. The exterior surface 114 of the annular projection 112 is configured to contact a respective surface on the proximal body 120. The annular projection 112 can have an interior surface 116 that is threaded. The female threads on the interior surface 116 are configured to mate with corresponding male threads on the bolt 130.

The proximal body 120 includes an annular projection 122 at its distal end. The annular projection 122 has an interior surface 124 that is cylindrical in shape. The interior surface 124 of the annular projection 122 is configured to contact the exterior surface 114 of the annular projection 112 of the distal stem 110. During alignment of the proximal body 120 to the distal stem 110, the interior surface 124 can slide past the exterior surface 114, so that the proximal body 120 can rotate about a longitudinal axis (A) of the annular projection 112 without translating away from the longitudinal axis (A). The proximal body 120 includes a bore 126, which is coaxial with the longitudinal axis (A). The most proximal portion of the bore 126 can be sized and shaped to accommodate a head of the bolt 130 so that, when installed, the bolt 130 extends fully into the bore 126. The bore 126 can include an annular wall 128, which is sized smaller than the head of the bolt 130.

The bolt 130 is elongated, with a head 132 at a proximal end and male threads 134 at or near a distal end. When the bolt 130 is installed, the threads 134 can engage the corresponding threads on the interior surface 116 of the annular projection 112 of the distal stem 110. The head 132 can be tightened against the annular wall 128 in the bore 126 of the proximal body 120. During and after installation, the bolt 130 is coaxial with the longitudinal axis (A). The bolt 130 can be tightened through the bore 126, using a suitably sized wrench, hex key, or other suitable tool.

In some examples, such as the modular hip stem 100 of FIG. 1, there is a cylindrical interface between the exterior surface 114 of the annular projection 112 of the distal stem 110 and the interior surface 124 of the annular projection 122 of the proximal body 120. As such, the proximal body 120 and the distal stem 110 can be pivoted with respect to each other. The pivoting motion is rotationally symmetric about the longitudinal axis (A). In other examples, this interface can be not purely cylindrical, but can include an asymmetry with respect to the longitudinal axis (A). For instance, the interface can have an elongated or elliptical cross-section, when viewed in a slice taken perpendicular to the longitudinal axis (A). Such an asymmetric cross-section can prevent pivoting between the proximal body 120 and the distal stem 110. In both the symmetric and asymmetric examples of FIG. 1, the interface has a cross-section taken in a slice perpendicular to the longitudinal axis (A), which can not vary for different locations along the longitudinal axis (A). In the example modular hip stem 100 of FIG. 1, the bolt 130 supplies a force that joins the proximal body 120 to the distal stem 110.

Figure 2:
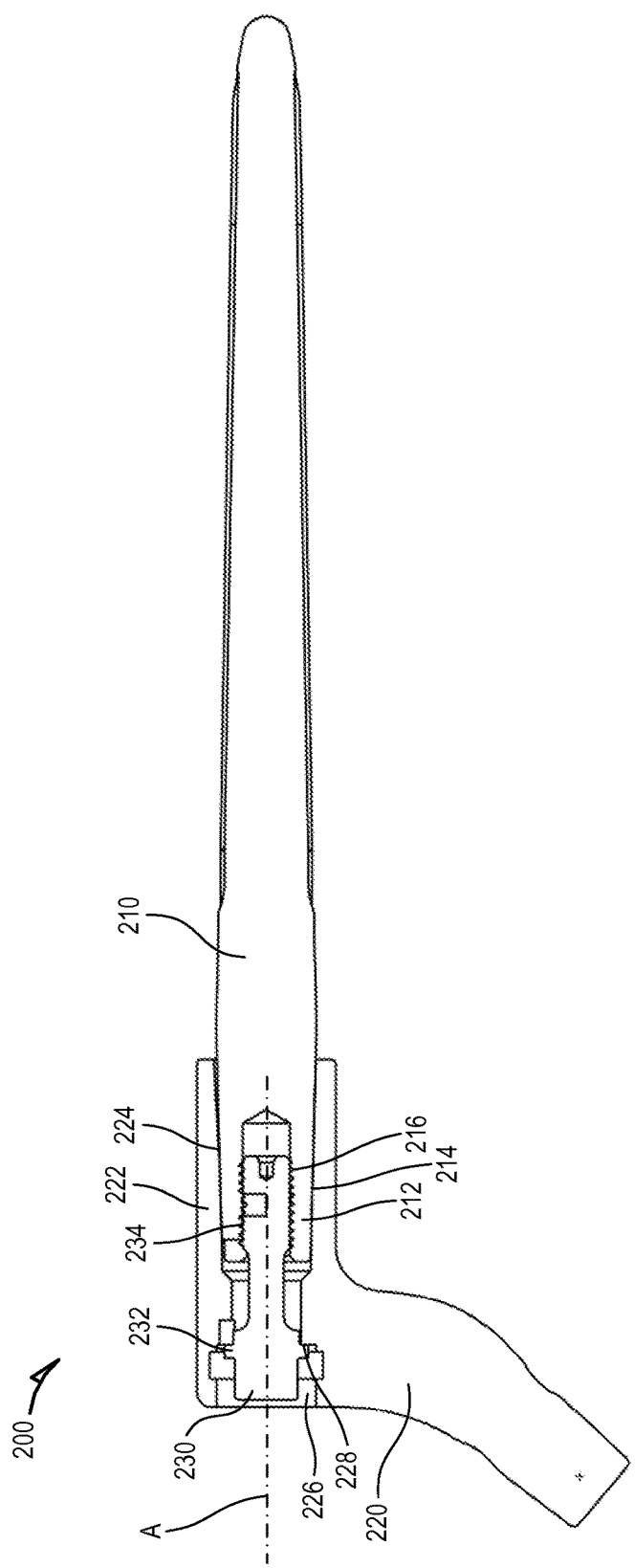
FIG. 2 is a side-view drawing of another exemplary modular hip stem, including a distal stem connected to another proximal body using a bolt. The interface between the distal stem and the proximal body is tapered.

FIG. 2 is a side-view drawing of another exemplary modular hip stem 200. The modular hip stem 200 includes a tapered interface between the exterior surface 214 of the annular projection 212 of the distal stem 210 and the interior surface 224 of the annular projection 222 of the proximal body 220. Both surfaces 214 and 224 include a taper and, together, form a tapered junction. The tapered junction can increase in cross-sectional size over the length of the longitudinal axis (A), from the proximal end of the junction to the distal end of the junction. In some of these examples, the tapered junction supplies a portion of a frictional force that joins the proximal body 220 to the distal stem 210; the bolt 230 supplies the remainder of the joining force. An example of a suitable taper is a Morse taper; other suitable tapers can also be used. The interior surface 216 having female threads, the bore 226, the annular wall 228, the bolt head 232, and the male threads 234 can be similar in structure and function to the similarly-numbered elements shown in FIG. 1.

In the exemplary modular hip stems 100, 200 shown in FIGS. 1 and 2, respectively, the bolt 130, 230 supplies some or all of the joining force between the proximal body 120, 220 and the distal stem 110, 210.

Figure 3:
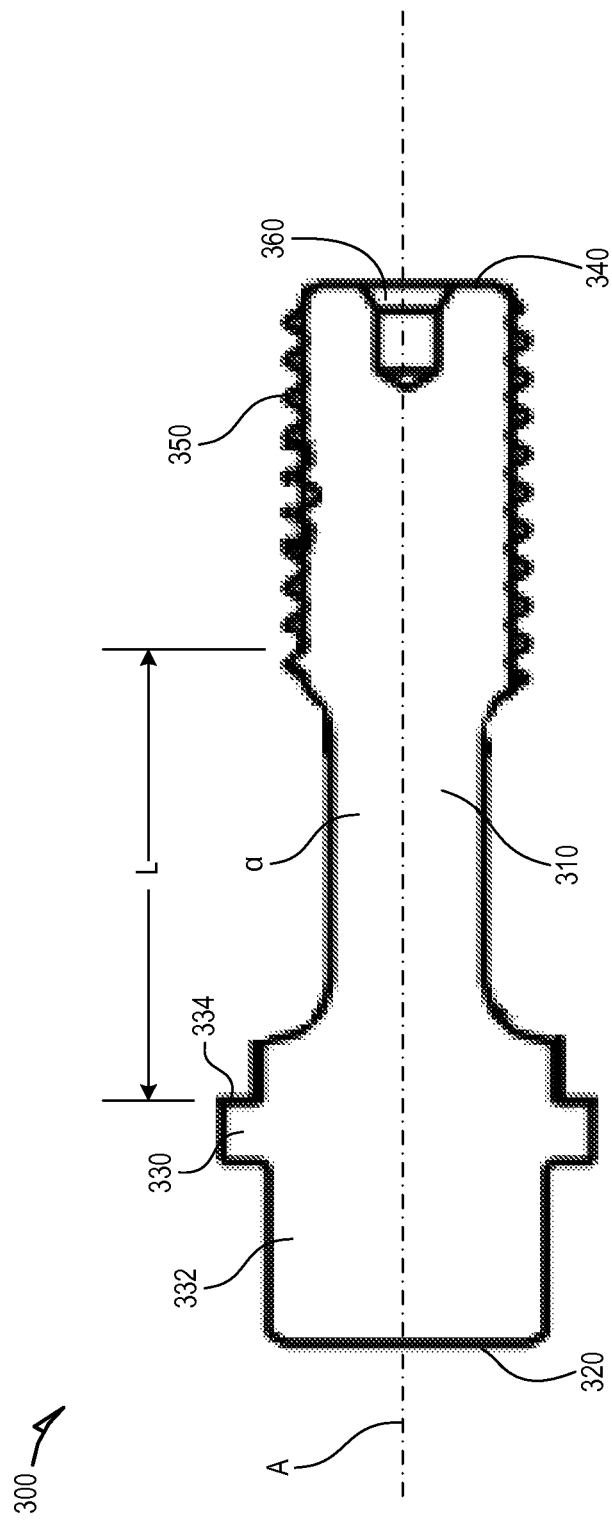
FIG. 3 is a side-view drawing of an exemplary bolt.

FIG. 3 is a side-view drawing of an exemplary bolt 300 suitable for use in the modular hip stems 100, 200 of FIGS. 1 and 2. The bolt 300 includes a proximal end 320, a distal end 340, and a longitudinal axis (A) extending from the proximal end 320 to the distal end 340.

The bolt 300 can include a head 330 at or near its proximal end 320. The head 330 can include a proximal portion 332 configured to be tightened by a suitable wrench, hex key, screwdriver or other tightening element that is removable from the bolt 300 and the hip stem. The tightening element can engage the head 330 of the bolt and can apply torque to the head 330 of the bolt 300 to rotate the bolt 300 around its longitudinal axis (A). In a cross-sectional slice taken perpendicular to the longitudinal axis (A), the proximal portion can have a polygonal shape, such as a triangle, a square, a pentagon, or a hexagon. Such a polygonal shape can be engaged by the opposing prongs of a wrench. Alternatively, the head 330 can include one or more depressions extending distally from the proximal end 320 of the bolt 300. The depressions can be shaped to engage a hexagonal key, a flat-head screwdriver, a Phillips-head screwdriver, a Torx head screwdriver, or another suitable tightening element. A distal end of the head 330 of FIG. 3 includes a distal-facing annular surface 334 that is pressed into contact with a corresponding surface on the proximal body. The annular surface 334 can radially extend farther from the longitudinal axis (A) than other portions of the bolt 300. The bolt 300 can, in some examples, be rotationally symmetric about the longitudinal axis (A) except for the proximal portion 332 of the head 330.

The bolt 300 can include one or more helically-shaped male threads 350 at or near its distal end 340. The threads 350 are configured to supply a frictional force against the corresponding female threads on the hip stem. The threads 350 can extend distally to the distal end 340 of the bolt 300 or can alternatively extend only to a location along the longitudinal axis proximal to the distal end 340 of the bolt 300. The distal end 340 of the bolt 300 can be typically flat and perpendicular to the longitudinal axis (A) of the bolt 300. The distal end 340 can optionally include a depression 360, which can accommodate a smaller screw head or other element that can extend proximally from the hip stem into the interior of the bolt 300. The distal end 340 can include a depression 360, which aids in machining the bolt, and allows the bolt to be centered on a lathe during manufacturing.

The bolt 300 can include a neck 310 that extends longitudinally from the head 330 to the threads 350. In some examples, the neck 310 can have a smaller cross-sectional diameter than the threads 350 and the head 330. In other examples, the neck 310 can have an equal or larger diameter than the threads and/or the head 330. In some examples, the neck 310 is unthreaded. In other examples, the neck 310 is threaded. In still other examples, the neck 310 is absent, and the threads 350 extend to the head 330. The shapes and configurations of the head 330, the threads 350, and the neck 310 shown in FIG. 3 and described herein are examples, and other suitable shapes and configurations can also be used. In the configuration of FIG. 3, a longitudinal length (L) of the bolt extends from the annular surface 334 to the threads 350.

The bolt 300 can be formed from a material, or an alloy of materials, that has a characteristic thermal expansion coefficient, denoted as a. The thermal expansion coefficient α can measure a change in volume or a change in longitudinal length as a function of temperature. The thermal expansion coefficient α can be positive so that as the temperature of the bolt increases, its volume and/or longitudinal length also increases. The bolt can be formed from a biocompatible material, such as at least one of cobalt, chromium, titanium, titanium alloys, stainless steel, and stainless steel alloys.

Figure 4:
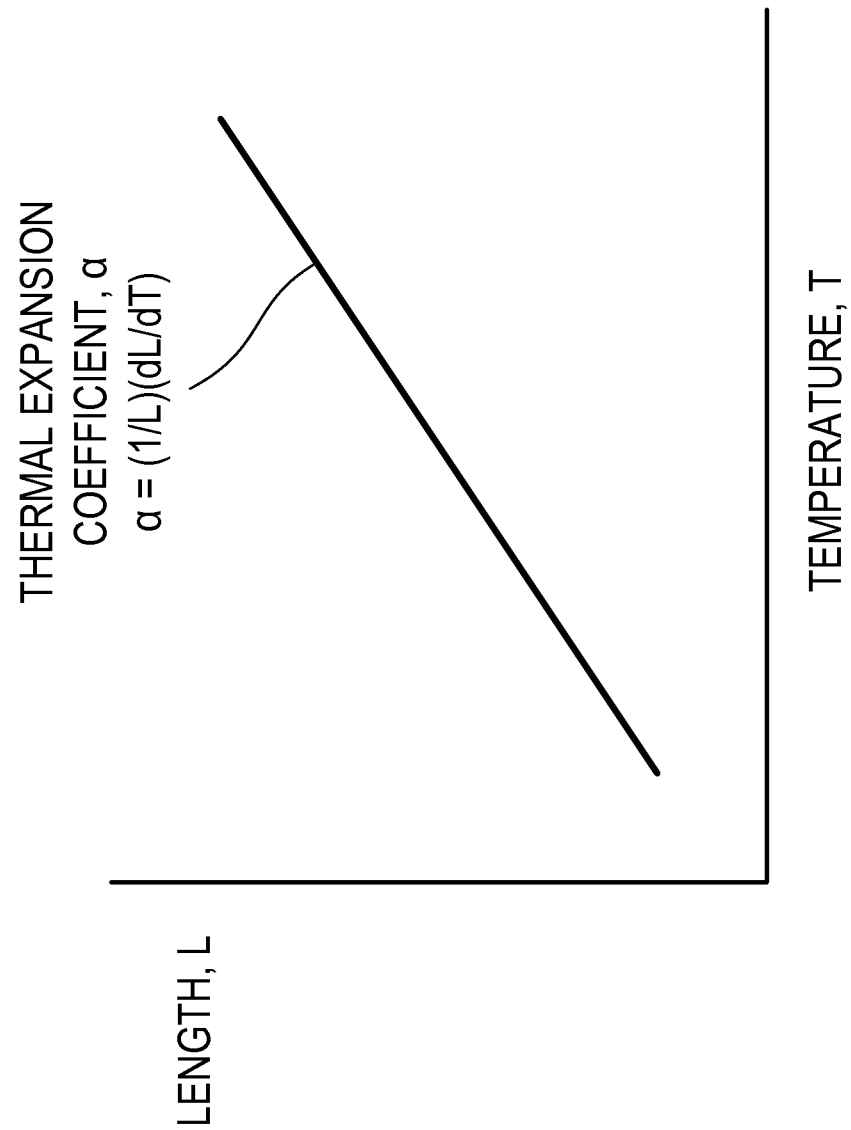
FIG. 4 is a plot of longitudinal length versus temperature, for the bolt of FIG. 3.

FIG. 4 is a plot of longitudinal length (L) versus temperature for the bolt 300 of FIG. 3. For a particular range of temperatures, such as a range that includes average human core body temperature, the length (L) can increase linearly or nearly linearly with temperature. The thermal expansion coefficient α of the bolt 300 describes the linear relationship as:

$$\alpha = (1/L)(dL/dT),$$

where L is the longitudinal length of the bolt 300, and dL/dT is the rate of change of the longitudinal length per unit change in temperature. The bolt length L shown in the plot of FIG. 4 assumes that the bolt is allowed to expand or contract freely as a function of temperature.

A fastening scheme can use the properties of thermal expansion to increase the holding strength of the bolt. For instance, a bolt can be installed or tightened at a particular temperature. The bolt can then be cooled to a lower temperature while remaining installed. If the bolt were left unconstrained, the bolt would longitudinally contract due to the change in temperature. In an installed state, where the longitudinal length of the bolt is fixed or constrained, the cooling to a lower temperature produces tensile stress in the bolt. The tensile stress pulls the longitudinal ends of the bolt closer together, and therefore increases the fastening strength, between a distal stem of a modular hip stem and a proximal body of the modular hip stem, provided by the bolt. In some cases, the fastening strength achieved by tightening at one temperature, then cooling the bolt to a lower temperature, can exceed the fastening strength achieved by solely tightening the bolt at the temperature at which the bolt is used.

Figure 5:
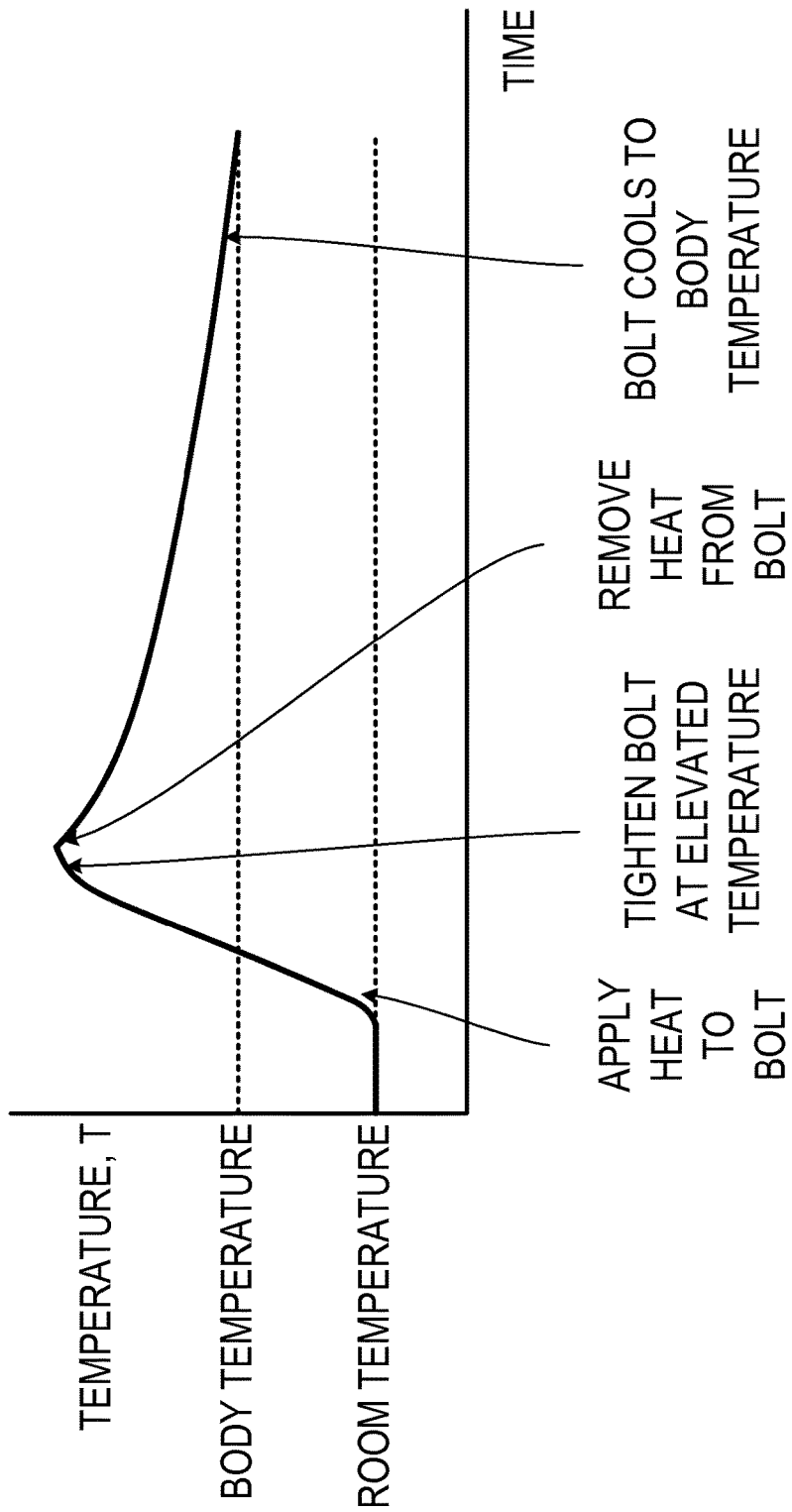
FIG. 5 is a plot of bolt temperature versus time, for the bolt of FIG. 3, for an exemplary surgical procedure.

FIG. 5 is a plot of bolt temperature (T) versus time for such an exemplary surgical procedure. In this procedure, the bolt is initially at room temperature, such as in a storage closet or cabinet. A practitioner then exposes the bolt to a heat source and heats the bolt to an elevated temperature that exceeds average human core body temperature (e.g., exceeding a temperature of 37° C., or 98.6° F.). The heat source can be outside the body of the patient, can be removable from the bolt, or can be made integral with the bolt. The practitioner tightens the bolt to a specified torque while the bolt is at the elevated temperature. In some examples, the bolt can be tightened while it is at a peak temperature; in other examples, the bolt can cool slightly from a peak temperature and can be tightened at the slightly cooled temperature, which still exceeds average human core body temperature.

The practitioner turns off the heat source, removes the heat source from the bolt, or removes the bolt from the heat source. The heat source can be removed or turned off before, during, or after the bolt is tightened. The practitioner allows the bolt to cool. In a surgical procedure in which the bolt is to be implanted within the human body, such as hip replacement surgery, the bolt cools to average human core body temperature. The bolt, in use, can be under tensile stress. For hip replacement surgery, the tensile stress in the bolt can force the proximal body and the distal stem closer against each other, with more force than can be obtained by tightening the bolt to the specified torque at room temperature or at average human core body temperature. This increase in force can desirably increase the holding strength of the bolt.

There are several ways to heat the bolt for the surgical procedure of FIG. 5. For instance, the bolt can be heated outside the body, such as in a warm liquid bath. The bolt can be heated in the bath to a specified elevated temperature, removed from the bath, then tightened in place while still at a temperature above the average human core body temperature. Alternatively, the bolt can include its own heating mechanism, so that it can be placed in the modular hip stem, can be heated while in place, and can be tightened at a suitable time at a suitable elevated temperature. Two exemplary heating mechanisms are shown in FIGS. 6 and 7.

Figure 6:
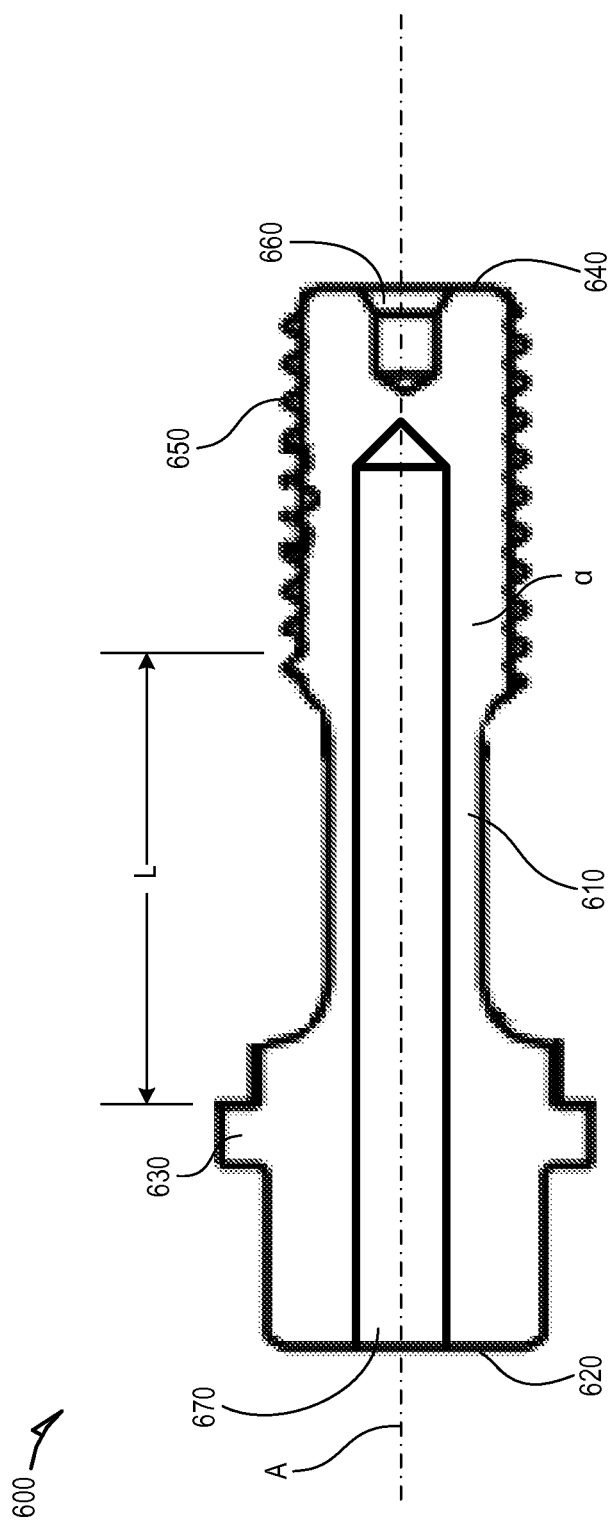
FIG. 6 is a side-view drawing of an exemplary bolt having a hollow interior.

FIG. 6 is a side-view drawing of an exemplary bolt 600 having a hollow interior. An elongated hollow cavity 670 extends within the bolt 600, generally parallel to the longitudinal axis (A), from a proximal end 620 of the bolt 600 toward a distal end 640 of the bolt 600. An external heater can be placed into the cavity 670 to heat the bolt 600 to a desired elevated temperature, and can be removed from the cavity before or after the bolt 600 is tightened. The head 630, neck 610, threads 650, and depression 660 can be similar in structure and function to corresponding similarly-numbered elements from FIG. 3.

Figure 7:
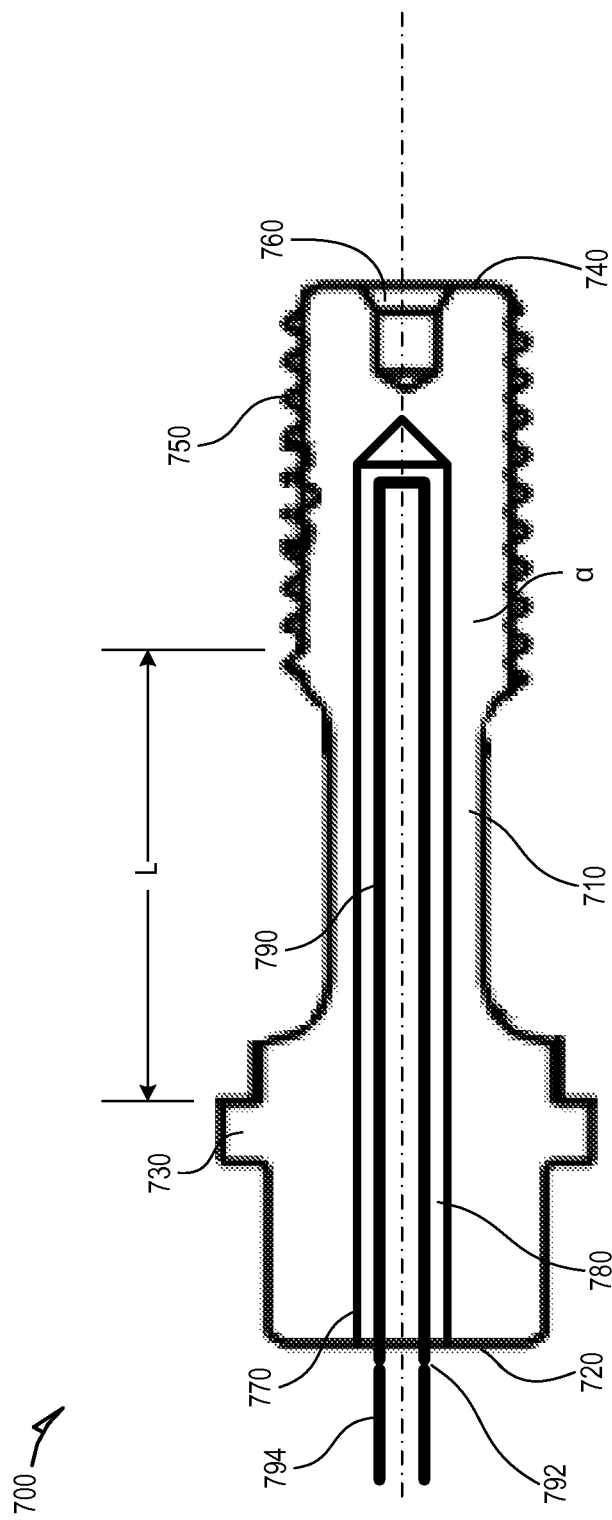
FIG. 7 is a side-view drawing of an exemplary bolt having an electrical resistive heater.

FIG. 7 is a side-view drawing of an exemplary bolt 700 having an electrical resistive heater 790. An internal volume 770 extends within the bolt 700, generally parallel to the longitudinal axis (A), from a proximal end 720 of the bolt 700 toward a distal end 740 of the bolt 700. An electrical resistive heater 790 is included within the internal volume 770. An electrically insulating, but thermally conductive, material 780 surrounds the electrical resistive heater 790 and fills the internal volume 770 around the electrical resistive heater 790.

One or more electrodes 794 are disposed outside the internal volume 770 and are configured to supply current to and from the electrical resistive heater 790. In some examples, the bolt 700 includes exactly two electrodes 794 extending therefrom, and the electrical resistive heater 790 has an electrical path extending from one of the two electrodes 794 to the other of the two electrodes 794. In some examples, at least one electrode 794 is detachable from the bolt 700 at a perforation 792. For these examples, each electrode 794 can include a respective perforation 792 at or near the proximal end 720 of the bolt so that a practitioner can tear the electrode 794 from the bolt 700 once the bolt 700 has been heated and tightened. The electrical resistive heater 790, the electrically insulating but thermally conductive material 780, and the electrodes 794 can all be formed from suitable biocompatible materials.

Figure 8:
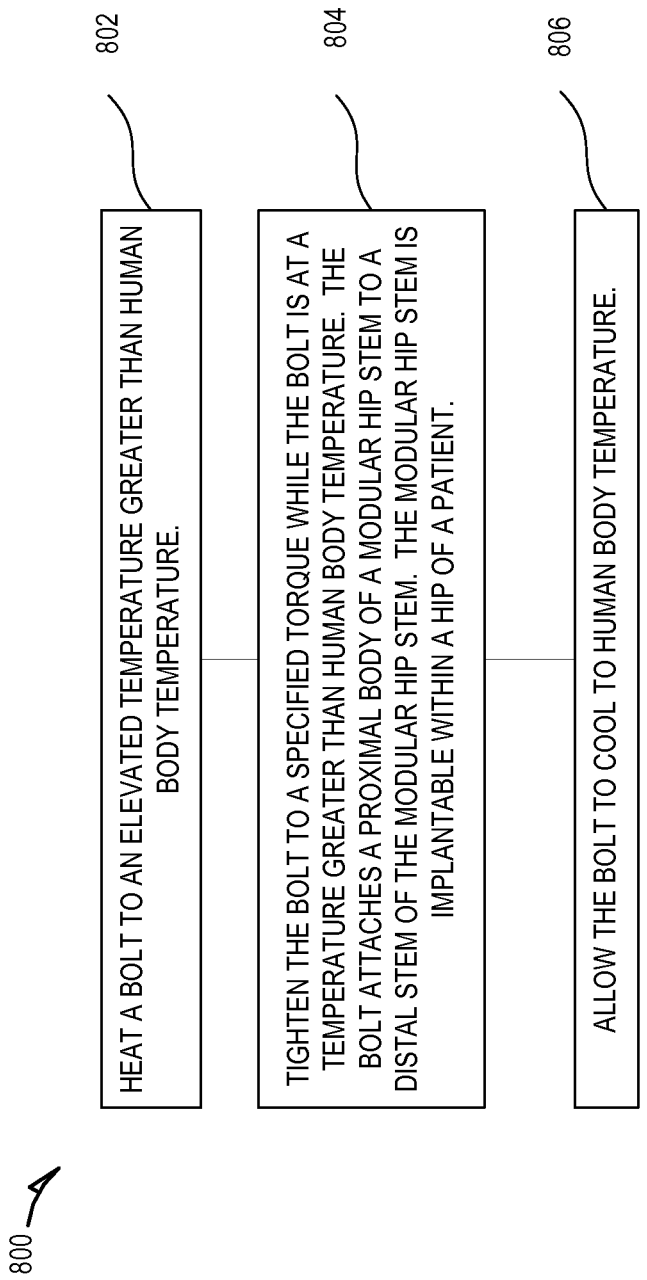
FIG. 8 is a flow chart of a method for assembling a modular hip stem.

FIG. 8 is a flow chart of a method 800 for assembling a modular hip stem. The method 800 can be executed using the distal stem 110, 210, the proximal body 120, 220, and the bolt 300, 600, 700. Step 802 includes heating a bolt to an elevated temperature greater than average human core body temperature. The heating step can occur before or after inserting the body into a lumen of the distal stem 110, 201 and the proximal body 120, 220. Step 804 includes tightening the bolt to a specified torque while the bolt is at a temperature greater than average human core body temperature. The bolt attaches a proximal body of a modular hip stem to a distal stem of the modular hip stem. The modular hip stem is implantable within a hip of a patient. Step 806 includes allowing the bolt to cool to average human core body temperature.

The above Detailed Description includes references to the accompanying drawings, which form a part of the Detailed Description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, assembly, device, kit, article, or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A modular hip stem, comprising:
a distal stem configured to be implanted within a femur of a patient;
a proximal body configured to attach to a proximal end of the distal stem;
a bolt configured to secure the proximal body to the distal stem, the bolt defining an internal volume extending longitudinally within the bolt from a proximal end of the bolt toward a distal end of the bolt;
an electrical resistive heater, disposed within the internal volume of the bolt, extending from the proximal end of the bolt toward the distal end of the bolt, and configured to heat the bolt to a temperature greater than average human core body temperature; and
a first electrode extending proximally from the electrical resistive heater to an exterior of the bolt, the first electrode configured to supply current to the electrical resistive heater, the first electrode attached to the electrical resistive heater at a narrowed portion of the first electrode, the narrowed portion being defined by a perforation, the first electrode configured to irreversibly detach from the electrical resistive heater by tearing at the narrowed portion when the first electrode is pulled away from the bolt.

2. The modular hip stem of claim 1, further comprising a second electrode extending proximally from the electrical resistive heater to the exterior of the bolt, the second electrode configured to accept current from the electrical resistive heater such that the electrical resistive heater has an electrical path extending from the first electrode to the second electrode.

3. The modular hip stem of claim 2, wherein the second electrode is attached to the electrical resistive heater at a second narrowed portion of the second electrode, the second electrode configured to detach from the electrical resistive heater at the second narrowed portion when the second electrode is pulled away from the bolt.

4. The modular hip stem of claim 2,
wherein the bolt includes a head at its proximal end; and
wherein the first electrode and the second electrode extend proximally from the head of the bolt.

5. The modular hip stem of claim 1,
wherein the electrical resistive heater is surrounded by an electric insulator; and
wherein the electrical resistive heater and the electric insulator are disposed in the internal volume of the bolt.

6. The modular hip stem of claim 5, wherein the internal volume of the bolt surrounds a longitudinal axis of the bolt.

7. The modular hip stem of claim 1, wherein the bolt includes a material having a positive thermal expansion coefficient.

8. The modular hip stem of claim 1, wherein, in a temperature region that includes average human core body temperature, the bolt includes a material causing its longitudinal length to increase linearly with an increase in temperature.

9. The modular hip stem of claim 1,
wherein the bolt includes a helical thread, engageable with the proximal end of the distal stem, at its distal end; and
wherein the bolt includes a head, engageable with the proximal body, at its proximal end.

10. The modular hip stem of claim 1, wherein the bolt is formed from a material including at least one of cobalt, chromium, titanium, titanium alloys, stainless steel, and stainless steel alloys.

11. A modular hip stem, comprising:
a distal stem configured to be implanted within a femur of a patient;
a proximal body configured to attach to a proximal end of the distal stem;
a bolt configured to secure the proximal body to the distal stem, the bolt defining an internal volume extending longitudinally within the bolt from a proximal end of the bolt toward a distal end of the bolt, the bolt including a head at its proximal end;

an electrical resistive heater, disposed within the internal volume of the bolt, extending from the proximal end of the bolt toward the distal end of the bolt, and configured to heat the bolt to a temperature greater than average human core body temperature;

a first electrode extending proximally from the electrical resistive heater, through the head of the bolt, to an exterior of the bolt, the first electrode configured to supply current to the electrical resistive heater, the first electrode attached to the electrical resistive heater at a first narrowed portion of the first electrode, the first narrowed portion being defined by a first perforation, the first electrode configured to irreversibly detach from the electrical resistive heater by tearing at the first narrowed portion when the first electrode is pulled away from the bolt;

a second electrode extending proximally from the electrical resistive heater, through the head of the bolt, to the exterior of the bolt, the second electrode configured to accept current from the electrical resistive heater such that the electrical resistive heater has an electrical path extending from the first electrode to the second electrode, the second electrode attached to the electrical resistive heater at a second narrowed portion of the second electrode, the second narrowed portion being defined by a second perforation, the second electrode configured to irreversibly detach from the electrical resistive heater by tearing at the second narrowed portion when the second electrode is pulled away from the bolt.

12. The modular hip stem of claim 11,
wherein the electrical resistive heater is surrounded by an electric insulator; and
wherein the electrical resistive heater and the electric insulator are disposed in the internal volume of the bolt.

13. The modular hip stem of claim 12, wherein the internal volume of the bolt surrounds a longitudinal axis of the bolt.

14. The modular hip stem of claim 11, wherein the bolt includes a material having a positive thermal expansion coefficient.

15. The modular hip stem of claim 11, wherein, in a temperature region that includes average human core body temperature, the bolt includes a material causing its longitudinal length to increase linearly with an increase in temperature.

16. The modular hip stem of claim 11,
wherein the bolt includes a helical thread, engageable with the proximal end of the distal stem, at its distal end; and
wherein the bolt includes a head, engageable with the proximal body, at its proximal end.

17. The modular hip stem of claim 11, wherein the bolt is formed from a material including at least one of cobalt, chromium, titanium, titanium alloys, stainless steel, and stainless steel alloys.

18. A modular hip stem, comprising:
a distal stem configured to be implanted within a femur of a patient;
a proximal body configured to attach to a proximal end of the distal stem;
a bolt configured to secure the proximal body to the distal stem, the bolt defining an internal volume extending longitudinally within the bolt from a proximal end of the bolt toward a distal end of the bolt, the internal volume of the bolt surrounding a longitudinal axis of the bolt, the bolt including a head at its proximal end, the bolt including a material having a positive thermal expansion coefficient;
an electrical resistive heater, positioned within the internal volume of the bolt, extending from the proximal end of the bolt toward the distal end of the bolt, and configured to heat the bolt to a temperature greater than average human core body temperature;
an electric insulator positioned in the internal volume of the bolt and surrounding the electrical resistive heater;
a first electrode extending proximally from the electrical resistive heater, through the head of the bolt, to an exterior of the bolt, the first electrode configured to supply current to the electrical resistive heater, the first electrode attached to the electrical resistive heater at a first narrowed portion of the first electrode, the first narrowed portion being defined by a first perforation, the first electrode configured to irreversibly detach from the electrical resistive heater by tearing at the first narrowed portion when the first electrode is pulled away from the bolt;
a second electrode extending proximally from the electrical resistive heater, through the head of the bolt, to the exterior of the bolt, the second electrode configured to accept current from the electrical resistive heater such that the electrical resistive heater has an electrical path extending from the first electrode to the second electrode, the second electrode attached to the electrical resistive heater at a second narrowed portion of the second electrode, the second narrowed portion being defined by a second perforation, the second electrode configured to irreversibly detach from the electrical resistive heater by tearing at the second narrowed portion when the second electrode is pulled away from the bolt.

19. The modular hip stem of claim 18,
wherein the bolt includes a helical thread, engageable with the proximal end of the distal stem, at its distal end; and
wherein the bolt includes a head, engageable with the proximal body, at its proximal end.

* * * * *